United States Patent

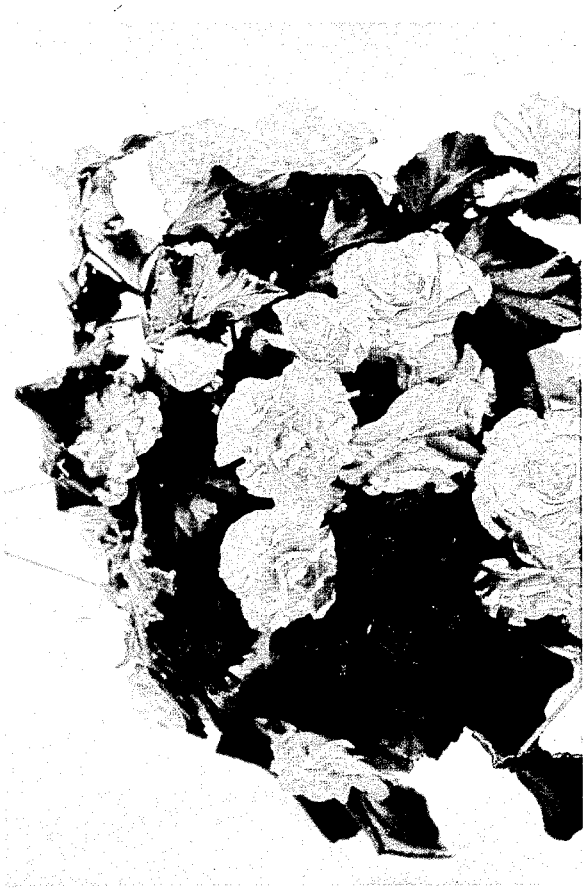

Plant Pat. 3,904

Patented June 8, 1976

3,904

BEGONIA PLANT

James C. Mikkelsen, Ashtabula, Ohio, assignor to Mikkelsens Inc., Ashtabula, Ohio

Filed May 5, 1975, Ser. No. 574,627

Int. Cl. A01h *5/00*

U.S. Cl. Plt.—68 1 Claim

The present invention relates to a new and distinctive variety of begonia plant known by the cultivar name Rose Elegance and botanically known as *Begonia elatior* (*hiemalis-Fotsch*). The new cultivar was discovered by me as a spontaneous sibling mutation (one of three) from a very bright deep rose red double flowering begonia identified by code number 8252 that was never commercialized. #8252 was a previous mutation from Aphrodite Rose, an unpatented, commercial cultivar. Asexual reproduction by stem and leaf cuttings has reproduced the unique features of the new cultivar through successive propagations.

The following characteristics distinguish the new begonia from both its parent and other begonias commercially known and used in the floriculture industry:

1. Compared to the deep rose red flowers of the parent variety the flower color of Rose Elegance is a bright, sparkling, light rose red. Tepals are darker at edges.

2. The flower size of Rose Elegance is 8–9 cm. in diameter compared to the flower size of 7–8 cm. of the parent variety.

3. A very distinguishing difference is the serrated and ruffled tepals of Rose Elegance compared to the normal rounded edges and flat tepals of the parent. Rose Elegance has the same camellia flower appearance as Elegance and Red Elegance, other mutations of the parent cultivar (#8252) are disclosed respectively in my pending application Ser. Nos. 574,626 and 574,628, filed May 5, 1975.

4. Of the three "Elegance" series, Rose Elegance is the least distinctive in the "flower-in-flower" characteristic, but there is an added depth to the size of the blooms.

5. Propagation can be by either vegetative stem cuttings or leaf cuttings. Leaf cuttings produce vegetative adventitious shoots that allow for greater manipulation by the grower in producing a sizeable flowering plant.

6. Vigorous, heavy stems similar to the Rieger Schwabenland types permits the grower to cultivate Rose Elegance as an upright plant when properly grown.

7. Flower quantity is similar to Aphrodite Rose, and the keeping quality in the house is superior to Aphrodite Rose.

8. Foliage is immune to mildew. Foliage color and quality are superior to Aphrodite Rose.

The accompanying colored photograph illustrates the overall appearance of this variety taken as a face view of the plant and showing the colors as true as it is reasonably possible to obtain in a colored reproduction of this type.

The following is a detailed description of my new begonia variety based on plants produced under commercial practices in Ashtabula, Ohio. Color references are made to the Royal Horticultural Society Colour Chart except where general color terms of ordinary dictionary significance are used.

Parentage: A spontaneous sibling mutation (one of three) that was found in begonia plant #8252 which was itself a mutation selected out of Aphrodite Rose.

Propagation: By vegetative top or stem cuttings that will root in 28–30 days. The most effective method to control flowering response is propagation by leaf cuttings that root in 30–35 days and eventually develop vegetative adventitious shoots from the base of the leaf petiole.

Rooting habit: Is considered near average for this type of begonia with fine, numerous, dendritic roots.

Plant form: Tends to be more upright than procumbent.

Habit of growth: Vigorous, fast growing, self branching.

Blooming habit: Is free flowering in all seasons.

Blooming season: Indeterminant by seasons. Easily manipulated by using vegetative plants from leaf cuttings as it is often difficult to obtain totally vegetative stem cuttings.

Foliage: Is of average quantity for this type of *elatior Begonia.*

Size: Considered moderately large measuring 10 cm. wide by 12 cm. long when plants are grown under commercial practices in Ashtabula, Ohio.

Shape: Cordate.

Texture: Smooth, waxy, thick, extreme protrusion of veins on underside of leaf.

Margin: Serrated; mature leaves revolute on underside of leaf.

Color: Young, upperside 137AB, underside 147C. Mature leaves, upperside, green between 137A and 147A, underside green 147C.

Disease resistance: Apparently immune to powdery mildew when grown in areas of mildew infected plants. Only very slightly susceptible to *Xanthomonas Begoniae.*

FLOWERS

Borne: On compound cyme—flowering continuously over a long period of time. Plants have been observed to be in flowering state for 12 months.

Quantity: Average for this type of begonia.

Buds: Flat—approximately 10–12 mm. in diameter before opening. Reverse of tepal before opening is light red.

Tepals: Edges are serrated, ruffled, center tepals form a swirl, color, red purple 58B–C.

Reproductive organs: None observed to date.

I claim:

1. A new and distinct cultivar of begonia plant characterized particularly by the combined features of light rose red tepal color and ruffled and serrated tepal form and "flower-in-flower" form that provides added depth to the size of the bloom; propagation by leaf cuttings which produce vegetative adventitious shoots; vigorous, heavy stems thereby permitting upright plant growth; superior keeping quality in the home, and by its foliage which is is excellent in quality and immune to powdery mildew and resistant to *Xanthomonas begoniae.*

No references cited.

ROBERT E. BAGWILL, Primary Examiner